(12) United States Patent
Szesni et al.

(10) Patent No.: US 12,172,148 B2
(45) Date of Patent: Dec. 24, 2024

(54) CATALYST COMPOSITION FOR SELECTIVE HYDROGENATION WITH IMPROVED CHARACTERISTICS

(71) Applicant: Sud-Chemie Inc., Louisville, KY (US)

(72) Inventors: Normen Szesni, Rosenheim (DE); Alfred Hagemeyer, Bad Aibling (DE); Frank Grossmann, Munich (DE); Richard Fischer, Bad Aibling (DE); Michael Urbancic, Louisville, KY (US); Claus Lugmair, San Jose, CA (US); Mingyong Sun, Louisville, KY (US); Hongyi C. Hou, San Jose, CA (US); David Michael Lowe, Sunnyvale, CA (US); Jennifer Boyer, Prospect, KY (US)

(73) Assignee: Sud Chemie, Inc., Louisville, KY (US)

( * ) Notice: Subject to any disclaimer, the term of this patent is extended or adjusted under 35 U.S.C. 154(b) by 6 days.

(21) Appl. No.: 16/694,149

(22) Filed: Nov. 25, 2019

(65) Prior Publication Data
US 2020/0101446 A1  Apr. 2, 2020

Related U.S. Application Data

(63) Continuation of application No. 13/276,403, filed on Oct. 19, 2011, now abandoned.

(51) Int. Cl.
| | | |
|---|---|---|
| *B01J 31/00* | (2006.01) | |
| *B01J 23/44* | (2006.01) | |
| *B01J 23/50* | (2006.01) | |
| *B01J 23/52* | (2006.01) | |
| *B01J 23/58* | (2006.01) | |
| *B01J 23/60* | (2006.01) | |
| *B01J 23/62* | (2006.01) | |
| *B01J 23/644* | (2006.01) | |
| *B01J 23/89* | (2006.01) | |
| *B01J 31/02* | (2006.01) | |
| *B01J 35/30* | (2024.01) | |
| *B01J 35/63* | (2024.01) | |
| *B01J 37/02* | (2006.01) | |
| *C07C 7/167* | (2006.01) | |
| *C10G 45/40* | (2006.01) | |
| *B01J 21/04* | (2006.01) | |
| *B01J 35/61* | (2024.01) | |
| *B01J 37/16* | (2006.01) | |

(52) U.S. Cl.
CPC ............ *B01J 23/44* (2013.01); *B01J 23/50* (2013.01); *B01J 23/52* (2013.01); *B01J 23/58* (2013.01); *B01J 23/60* (2013.01); *B01J 23/62* (2013.01); *B01J 23/626* (2013.01); *B01J 23/628* (2013.01); *B01J 23/6447* (2013.01); *B01J 23/8926* (2013.01); *B01J 31/0277* (2013.01); *B01J 31/0279* (2013.01); *B01J 31/0284* (2013.01); *B01J 35/397* (2024.01); *B01J 35/633* (2024.01); *B01J 37/0201* (2013.01); *B01J 37/024* (2013.01); *C07C 7/167* (2013.01); *C10G 45/40* (2013.01); *B01J 21/04* (2013.01); *B01J 35/612* (2024.01); *B01J 37/16* (2013.01); *B01J 2231/645* (2013.01); *B01J 2531/824* (2013.01); *C10G 2400/20* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,404,124 | A | 9/1983 | Johnson et al. |
| 4,409,410 | A | 10/1983 | Cosyns et al. |
| 4,519,951 | A | 5/1985 | Qualeatti et al. |
| 4,835,131 | A | 5/1989 | DeJong |
| 4,837,189 | A | 6/1989 | Simon et al. |
| 4,977,126 | A | 12/1990 | Mauldin et al. |
| 5,012,027 | A | 4/1991 | Abrevaya et al. |
| 5,089,245 | A | 2/1992 | Eyman et al. |
| 5,648,576 | A | 7/1997 | Nguyen Than et al. |
| 5,672,734 | A | 9/1997 | Abel et al. |
| 5,693,585 | A | 12/1997 | Benazzi et al. |
| 6,040,263 | A | 3/2000 | Mussmann et al. |
| 6,355,596 | B2 | 3/2002 | Hu et al. |
| 6,465,391 | B1 | 10/2002 | Cheung et al. |
| 6,603,038 | B1 | 8/2003 | Hagemeyer et al. |

(Continued)

FOREIGN PATENT DOCUMENTS

| | | | |
|---|---|---|---|
| CA | 2170330 | A1 | 8/1997 |
| CA | 2442288 | A1 | 10/2002 |
| CN | 1538876 | A | 10/2004 |
| CN | 101045213 | A | 10/2007 |
| DE | 3119850 | A1 | 2/1982 |
| DE | 19734974 | A1 | 2/1999 |
| DE | 10315215 | A1 | 10/2004 |
| DE | 102006019460 | A1 | 10/2007 |
| DE | 102007025317 | A1 | 12/2008 |
| DE | 102007025362 | A1 | 12/2008 |
| DE | 102007025443 | A1 | 12/2008 |
| EP | 0064301 | A1 | 11/1982 |
| EP | 0551019 | A1 | 7/1993 |

(Continued)

OTHER PUBLICATIONS

Arras, J., "Einfluss Ionischer Flüssigkeiten mit funktionalisierten Kationen auf die palladiumkatalysierte Flüssig-phasenhydrierung von Citral", Chemie Ingenieur Technik (2009), 81, No. 12, pp. 2007-2011 (Abstract only).

(Continued)

*Primary Examiner* — Yun Qian

(74) *Attorney, Agent, or Firm* — Buchanan Ingersoll & Rooney PC

(57) ABSTRACT

This invention relates to heterogeneous catalysts useful for selective hydrogenation of unsaturated hydrocarbons, comprising palladium and optionally a promoter, supported on a substrate, having an uncoated BET surface area of ≤9 m²/g, the surface being coated with an ionic liquid. Also described are methods of making the catalysts and methods of selective hydrogenation of acetylene and/or dienes in front-end mixed olefin feed streams.

13 Claims, No Drawings

(56) References Cited

U.S. PATENT DOCUMENTS

| | | | |
|---|---|---|---|
| 6,969,693 | B2 | 11/2005 | Sauvage et al. |
| 7,026,266 | B2 | 4/2006 | Chaudhari et al. |
| 7,381,845 | B2 | 6/2008 | Weiskopf et al. |
| 7,799,373 | B2 | 9/2010 | Sachweh et al. |
| 7,799,730 | B2 | 9/2010 | Ringer et al. |
| 8,247,340 | B2 | 8/2012 | Johnson et al. |
| 8,334,232 | B2 | 12/2012 | Jess et al. |
| 2002/0198100 | A1 | 12/2002 | Mehnert et al. |
| 2004/0059153 | A1 | 5/2004 | Magna et al. |
| 2004/0235650 | A1 | 11/2004 | Saleh et al. |
| 2005/0033102 | A1 | 2/2005 | Randolph et al. |
| 2005/0181940 | A1 | 8/2005 | Wang et al. |
| 2006/0217579 | A1 | 9/2006 | Bailey |
| 2008/0255257 | A1 | 10/2008 | Kuipers et al. |
| 2008/0269533 | A1 | 10/2008 | Chang et al. |
| 2009/0256113 | A1 | 10/2009 | Borchers et al. |
| 2009/0264691 | A1 | 10/2009 | Jess et al. |
| 2010/0190638 | A1 | 7/2010 | Hagemeyer et al. |
| 2010/0197488 | A1 | 8/2010 | Hagemeyer et al. |
| 2010/0217052 | A1 | 8/2010 | Ungar et al. |
| 2010/0273644 | A1 | 10/2010 | Hagemeyer et al. |
| 2011/0065950 | A1 | 3/2011 | Riisager et al. |
| 2011/0152064 | A1 | 6/2011 | Keshavan et al. |
| 2011/0166010 | A1 | 7/2011 | Hagemeyer et al. |
| 2011/0217781 | A1 | 9/2011 | Johnson et al. |
| 2013/0041193 | A1 | 2/2013 | Szesni et al. |
| 2013/0102819 | A1 | 4/2013 | Szesni et al. |

FOREIGN PATENT DOCUMENTS

| | | |
|---|---|---|
| EP | 0553815 A1 | 8/1993 |
| EP | 0780155 A1 | 6/1997 |
| EP | 1120159 A1 | 8/2001 |
| EP | 1364936 A1 | 11/2003 |
| FR | 2628014 A1 | 9/1989 |
| JP | 2009502458 A | 1/2009 |
| WO | 9814274 A1 | 4/1998 |
| WO | 9903163 A1 | 1/1999 |
| WO | 0029108 A1 | 5/2000 |
| WO | 0132308 A1 | 5/2001 |
| WO | 02078842 A1 | 10/2002 |
| WO | 02094740 A2 | 11/2002 |
| WO | 02096557 A1 | 12/2002 |
| WO | 02098560 A1 | 12/2002 |
| WO | 2005016855 A2 | 2/2005 |
| WO | 2005123253 A1 | 12/2005 |
| WO | 2006114320 A1 | 11/2006 |
| WO | 2006122563 A1 | 11/2006 |
| WO | 2007124896 A1 | 11/2007 |
| WO | 2008145387 A2 | 12/2008 |
| WO | 2008145388 A1 | 12/2008 |
| WO | 2008145391 A2 | 12/2008 |
| WO | 2011028466 A2 | 3/2011 |
| WO | 2011029691 A1 | 3/2011 |
| WO | 2011050953 A2 | 5/2011 |

OTHER PUBLICATIONS

Arras, J., "Einfluss Ionischer Flüssigkeiten mit funktionalisierten Kationen auf die palladiumkatalysierte Flüssig-phasenhydrierung von Citral", Chemie Ingenieur Technik (2009), 81, No. 12, pp. 2007-2011.

Arras et al., "How a Supported Metal is Influenced by an Ionic Liquid: In-Depth Characterization of SCILL-Type Palladium Catalysts and Their Hydrogen Adsorption", J. Phys. Chem. C 2010, 114, pp. 10520-10526.

Arras et al., "The Promoting Effect of a Dicyanamide Based Ionic Liquid in the Selective Hydrogenation of Citral", Chem. Commun., 2008, pp. 4058-4060.

Arras et al., "Regioselective Catalytic Hydrogenation of Citral with Ionic Liquids as Reaction Modifiers", Green Chem., 2009, 11, pp. 716-723.

Arras et al., "Supported Ruthenium Catalysed Selective Hydrogenation of Citral in Presence of [NTf2]-based Ionic Liquids", Applied Catalysis A: General 371 (2009), pp. 73-77.

Baudoux et al., "Development of New SILP Catalysts using Chitosan as Support", Green Chem., 2007, 9, pp. 1346-1351.

Breitenlechner et al., "Solid Catalysts on the Basis of Supported Ionic Liquids and Their Use in Hydroamination Reactions", Journal of Molecular Catalysis A: Chemical 214, (2014), pp. 175-179.

DeCastro et al., "Immobilized Ionic Liquids as Lewis Acid Catalyst for the Alkylation of Aromatic Compounds with Dodecene", Journal of Catalysis, 196, (2000), pp. 86-94.

Dullius et al., "Selective Catalytic Hydrodimerization of 1,3-Butadiene by Palladium Compounds Dissolved in Ionic Liquids", Organometallics, 1998, 17, pp. 815-819.

Eigenberger, G., "Fixed-bed Reactors", Ullman's Encyclopedia, 6th Edition, 2000, Electronic Release, Chapter Fixed-bed Rector's, Par. 2: Catalyst for Fixed-bed Reactors, 77 pages.

Fow et al., "Enhanced Enantioselectivity of Chiral Hydrogenation Catalysts after Immobilisation in Thin Films of Ionic Liquids", Journal of Molecular Catalysis A: Chemical 279, (2008), pp. 239-247.

Gallezot, Fundamental Aspects of Heterogeneous Catalytic Hydrogenation Encyclopedia of Catalysis, John Wiley & Sons, available online Jul. 15, 2002.

Gu et al., "Ionic Liquids-based Catalysis with Solids: State of the Art", Adv. Synth. Catal., 2009, 351, pp. 817-847.

Haber et al., "Manual of Methods and Procedures for Catalyst Characterization", Pure & Applied Chem., vol. 67, Nos. 8/9, 1995, pp. 1257-1306.

Hagiwara et al., "Supported Ionic Liquid Catalyst (Pd-SILC) for Highly Efficient and Recyclable Suzuki-Miyaura Reaction", Chem. Commun., 2007, pp. 2838-2840.

Haumann et al., "Continuous Gas-Phase Hydroformylation of 1-Butene using Supported Ionic Liquid Phase (SILP) Catalysts", Adv. Synth. Catal., 2007, 349, pp. 425-431.

Herrmann et al., "High-performance Supported Catalysts with an Ionic Liquid Layer for the Selective Hydrogenation of Acetylene", Chem. Commun., 2011, 47, pp. 12310-12312.

Huang et al., "Pd Nanoparticles Immobilized on Molecular Sieves by Ionic Liquids: Heterogeneous Catalysts for Solvent-Free Hydrogenation", Angew. Chem. Int. Ed., 2004, 43, pp. 1397-1399.

International Search Report and Written Opinion for International Application PCT/EP2010/006561, dated Nov. 23, 2011, 26 pages.

Joni et al., "Development of a Supported Ionic Liquid Phase (SILP) Catalyst for Slurry-Phase Friedel-Crafts Alkylations of Cumene", Adv. Synth, Catal., 2009, 351, pp. 423-431.

Kernchen et al., "Solid Catalyst with Ionic Liquid Layer (SCILL)—A New Concept to Improve Selectivity illustrated by Hydrogenation of Cyclooctadiene", Chem. Eng. Technol., 2007, 30, No. 8, pp. 985-994.

Kiwi-Minsker et al., "Structured Catalytic Wall Microreactor for Efficient Performance of Exothermic", Chemical Engineering and Processing, 49, (2010), pp. 973-978.

Leofanti et al., "Surface Area and Pore Texture of Catalysts", Catalysis Today, 41, (1998), pp. 207-219.

Mehnert et al., "Supported Ionic Liquid Catalysis—A New Concept for Homogeneous Hydroformulation Catalysis", J. Am. Chem. Soc., 2002, 124, pp. 12932-12933.

Mehnert et al., "Supported Ionic Liquid Catalysis Investigated for Hydrogenation Reactions", The Royal Society of Chemistry, 2002, pp. 3010-3011.

Mehnert, C., "Supported Ionic Liquid Phases" Chemistry: A European Journal, 2005, 11, pp. 50-56.

Mikkola et al., "Effect of Internal Diffusion in Supported Ionic Liquid Catalysts: Interaction with Kinetics", Ind. Eng. Chem. Res., 2007, 46, pp. 3932-3940.

Mikkola et al., "Supported Ionic Liquids Catalysts for Fine Chemicals: Citral Hydrogenation", Green Chem., 2006, 8, pp. 197-205.

Riisager et al., "First Application of Supported Ionic Liquid Phase (SILP) Catalysis for Continuous Methanol Carbonylation", Chem. Commun., 2006, pp. 994-996.

(56) References Cited

OTHER PUBLICATIONS

Riisager et al., "Supported Ionic Liquids: Versatile Reaction and Separation Media", Topics in Catalysis, vol. 40, Nos. 1-4, Nov. 2006, pp. 91-102.
Ruta et al., "Pd Nanoparticles in a Supported Ionic Liquid Phase: Highly Stable Catalysts for Selective Acetylene Hydrogenation Under Continuous-flow Conditions", J. Phys. Chem. C, 2008, 112(46), 17814-17819.
Schwab et al., "Ruthenium-Catalyzed Selective Hydrogenation of Benzene to Cyclohexene in the Presence of an Ionic Liquid", Angew. Chem. Int. Ed., 2011, 50, pp. 10453-10456.
Sievers et al., "Formation of Solvent Cages around Organometallic Complexes in Thin Films of Supported Ionic Liquid", J. Am. Chem. Soc., 2006, 128, pp. 13990-13991.
Sobota et al., "Ligand Effects in SCILL Model Systems: Site-Specific Interactions with Pt and Pd Nanoparticles", Adv. Mater., 2011, 23, pp. 2617-2621.
Steinrück et al., "Surface Science and Model Catalysis with Ionic Liquid-Modified Materials", Adv. Mater., 2011, pp. 2571-2587.
Tao et al., "Nanoparticles Immobilized on Sepiolite by Ionic Liquids: Efficient Catalysts for Hydrogenation of Alkenes and Heck Reactions", Green Chem., 2009, 11, pp. 96-101.
Virtanen et al., "Towards One-pot Synthesis of Menthols from Citral: Modifying Supported Ionic Liquid Catalysts (SILCAs) with Lewis and Brønsted Acids" Journal of Catalysis, 263, (2009), pp. 209-219.
Wasserscheid, P., "Ionic Liquids-new "Solutions" for Transition Metal Catalysis", Angew Chem. Int. Ed., 2000, 39, pp. 3772-3789.
Wasserscheid, P., "Ionische Flüssigkeiten—neue Lösungen für die Übergangmetallkatalyse", Agnew. Chem., 2000, 112, pp. 3926-3945.
Zeolyst Product List as of Mar. 24, 2005, available through Internet Archive.org, 3 pages.
Entire patent prosecution history of U.S. Appl. No. 13/504,276, filed Oct. 15, 2012, entitled, "Method for Producing a Composite Material".
Non Final Office Action for U.S. Appl. No. 16/681,196, mailed Aug. 2, 2021, 25 pages.
Final Office Action for U.S. Appl. No. 16/681,196, dated Oct. 27, 2021, 20 pages.
Non-Final Office Action for U.S. Appl. No. 16/681,196, mailed May 2, 2022, 15 pages.
Final Office Action for U.S. Appl. No. 16/681,196, mailed Aug. 24, 2022, 11 pages.
Non Final Office Action for U.S. Appl. No. 16/681,196, mailed Nov. 1, 2022, 18 pages.
Final Office Action for U.S. Appl. No. 16/681,196, mailed Feb. 17, 2023, 26 pages.
Bergwerff et al., "Monitoring Transport Phenomena of Paramagnetic Metal-Ion Complexes Inside Catalyst Bodies with Magnetic Resonance Imaging", Chem. Eur. J., 2008, vol. 14, pp. 2363-2374.
Non Final Office Action for U.S. Appl. No. 16/681,196, mailed Sep. 22, 2023, 19 pages.
Office Action issued by the U.S. Patent and Trademark Office in the U.S. Appl. No. 16/681,196, mailed Feb. 2, 2024, U.S. Patent and Trademark Office, Alexandria, VA. (16 pages).
Advisory Action Before the Filing of an Appeal Brief issued by the U.S. Patent and Trademark Office in the U.S. Appl. No. 16/681,196, mailed Apr. 1, 2024, U.S. Patent and Trademark Office, Alexandria, VA. (3 pages).
Notice of Allowance issued by the U.S. Patent and Trademark Office in U.S. Appl. No. 16/681,196, mailed Sep. 12, 2024, U.S. Patent and Trademark Office, Alexandria, VA. (21 pages).

CATALYST COMPOSITION FOR SELECTIVE HYDROGENATION WITH IMPROVED CHARACTERISTICS

CROSS-REFERENCE TO RELATED APPLICATIONS

This application is a continuation of U.S. application Ser. No. 13/276,403, filed Oct. 19, 2011, the contents of which are incorporated herein by reference in its entirety.

FIELD OF THE INVENTION

The present invention is related to a catalyst composition for selective hydrogenations, for example for the selective hydrogenation of acetylene in the gaseous phase, comprising a heterogeneous catalyst with a BET surface area of ≤9 m$^2$/g and an ionic liquid applied to the surface of the same. The catalyst composition has improved characteristics such as, for example, improved selectivity in favor of the desired product and better thermal stability.

BACKGROUND OF THE INVENTION

Ethylene and propylene are important monomers for the production of plastics, such as for example polyethylene or polypropylene. Ethylene and propylene are primarily derived from petroleum and petroleum products by means of thermal or catalytic cracking of hydrocarbons. The ethylene or propylene derived with the aid of the cracking process does, however, contain an undesirably high proportion of acetylenic compounds such as acetylene or methyl acetylene (propyne), which can negatively influence downstream ethylene or propylene polymerization. Therefore prior to polymerization the ethylene or propylene must be freed from acetylenic compounds as far as possible.

Typically for the polymerization of ethylene the acetylene concentration must, for example, be reduced to a value of below 1 ppm. For this the acetylene is selectively hydrogenated into ethylene. High requirements are placed on the catalyst and the hydrogenation process. On the one hand, the acetylene must be removed as completely as possible by transformation into ethylene, while the hydrogenation of ethylene into ethane must be prevented, hence the term "selective hydrogenation". In order to ensure this result, the hydrogenation is carried out within a temperature range that is delimited by the so-called "clean-up" temperature and the so-called "run-away" temperature. In the present context the "clean-up" temperature is understood as the temperature from which an appreciable hydrogenation of acetylene into ethylene is observed, while "run-away" temperature is understood as the temperature at which an appreciable hydrogenation of ethylene into ethane commences. The said temperatures can be determined in that the hydrogen consumption of a defined gas mixture containing acetylene, ethylene, and hydrogen is, for example, measured depending on the temperature.

Palladium shell catalysts, often using silver as a promoter, are primarily used as commercial catalysts for the selective hydrogenation of acetylene into ethylene in hydrocarbon streams. The palladium and the silver are supported on an inert, temperature-resistant substrate. The production of these catalysts is carried out in such a way that suitable salts of palladium and silver, for example palladium nitrate and silver nitrate, are applied to a substrate in form of an aqueous solution (impregnation). The impregnation can take place during separate steps with a palladium compound solution and a silver compound solution. It is, however, also possible to apply the solution of palladium compounds and the solution of silver compounds to the substrate simultaneously during a single impregnation step. The impregnated substrate is then calcined to transform the silver into silver oxide, or the palladium into palladium oxide, and is then subjected to a reduction in order to transfer the catalyst into the active form. During the reaction the silver and palladium are assumed to be transferred into the oxidation state "zero".

DE 31 19 850 A1 describes a method for the selective hydrogenation of a diolefin with at least 4 carbon atoms in a hydrocarbon mixture. Hydrogenation takes place with hydrogen on a catalyst containing palladium and silver. The silver/palladium weight ratio of the catalyst is 0.7:1 to 3:1. The production of the catalyst is by way of co-impregnation of a substrate with an aqueous solution of palladium and silver salts.

U.S. Pat. No. 5,648,576 A describes a method for the selective gaseous phase hydrogenation of acetylenic hydrocarbons ($C_2$-$C_3$) into the corresponding ethylenic hydrocarbons. The production of the catalyst is realized by co-impregnating the substrate with an aqueous solution of the respective metal salts.

EP 0 064 301 A1 offers a catalyst for the selective gaseous phase hydrogenation of acetylene. The production of the catalyst is realized by means of a two-step application of palladium and silver.

EP 0 780 155 A1 describes the production of hydrogenation catalysts, whereby solutions of palladium nitrate and silver nitrate in a nitrogenous acid are used for the impregnation of the substrate.

Apart from the Pd/Ag catalysts described above, a number of further palladium based catalyst are described, which also provide improved selectivity and sometimes also improved activity; the same include Pd/Zn, Pd/Cd, Pd/Ga and Pd/Au. The latter catalyst family is characterized primarily by a high "run-away" temperature.

According to the definition of Wasserscheid and Keim in "Angewandte Chemie" 2000, 112, pages 3926-3945, ionic liquids are salts, i.e. compounds of anions and cations that are externally neutral, which melt at low temperatures, usually at temperatures of below 100° C. Ionic liquids are therefore already liquid at low temperatures. In addition they are generally not flammable and have an extremely low vapor pressure. Due to the high variation range of the structure of their cations and anions, their physical and chemical characteristics can be varied over a broad range.

The concept of coating heterogeneous catalysts with small quantities of an ionic liquid has already been described by Jess et al. and Claus et al. [U. Kernchen, B. Etzold, W. Korth, A. Jess, Chem. Eng. Technol. 2007, 30, 985-994; J. Arras, M. Steffan, Y. Shayeghi, P. Claus, Chem. Commun. 2008, 4058-4060]. In both cases an improved selectivity towards the desired product in the target reaction of the hydrogenation of citral or the hydrogenation of diolefins could be achieved than is possible with the uncoated catalyst. This catalyst family has also been named as SCILL—Solid Catalyst with Ionic Liquid Layer—catalysts by the authors.

US 2008/0269533 A1 describes the selective mono-hydrogenation of conjugated dienes with the aid of supported Pd nanoparticles coated with ionic liquids.

International patent application WO2007/124 896 relates to heterogeneous catalysts having a BET surface area of preferably 10 to 300 m$^2$/g. These catalysts may be covered with an ionic liquid and are used for the selective hydrogenation of unsaturated cyclic compounds.

A catalyst system for the selective hydrogenation of acetylene in the simultaneous presence of ethylene comprising a heterogeneous catalyst coated with ionic liquid has also already been described [M. Ruta, G. Laurenczy, P. J. Dyson, L. Kiwi-Minsker, J. Phys. Chem. C 2008, 112, 17814-17819]. However, these catalysts are prepared with support materials that are not suitable for industrial use, as the production of the same is too costly. The described turnovers are also far from realizable.

With all of the examples described so far support materials with a high specific surface area and a suitable pore volume were used. In order to achieve an even coating of the entire catalyst surface, and thus the best possible effect (selectivity increase etc.) a relatively large quantity of ionic liquid is required (10-17 wt. % in relation to the initial weight of the heterogeneous catalyst). This often results in a substantial pore filling of the catalyst and the reduced activity connected with the same. Ionic liquids are also expensive, which results in substantial additional costs for the overall catalyst formulation.

SUMMARY OF THE INVENTION

There remains a need for further improving the selectivity of Pd/promoter catalysts for the hydrogenation of acetylenic hydrocarbons, while maintaining or even increasing catalyst activity.

It is therefore the object of this invention to provide a catalyst with high selectivity and activity for the hydrogenation of acetylenic hydrocarbons.

Surprisingly it has been found that conventional heterogeneous catalysts with a BET surface area of ≤9 m$^2$/g which are coated with a small amount of an ionic liquid have improved characteristics, such as improved selectivity in the hydrogenation of unsaturated hydrocarbons while retaining high activity.

With the catalyst system of the invention, known pre-formulated catalysts for the transformation of acetylene into ethylene with a BET surface area of ≤9 m$^2$/g are coated with one (or more) ionic liquid(s). The resulting catalyst formulations have a very high selectivity during the hydrogenation of acetylene in ethylene rich gas streams and are further surprisingly characterized by a higher "run-away" temperature. The catalyst formulations of the invention further may use very small quantities of ionic liquid (in the range of ≤3% by weight of the catalyst) to achieve these advantageous effects. The loss of catalyst activity is very small.

DETAILED DESCRIPTION OF THE INVENTION

The pre-formulated catalysts used for coating are, as already described above, supported palladium shell catalysts which preferably comprise at least one further promoter such as for example silver, gold, zinc, tin, lead, gallium, cadmium, copper, bismuth, or potassium. Preferred promoters are Ag, Au and Zn. Preferred metal or metal-alloy shell thicknesses are between 100 and 500 μm. The Pd metal content in relation to the total weight of the catalyst is between 10 and 1000 ppm, preferably between 50 and 500 ppm. For the desired target reaction the catalysts are used either as shaped bodies such as for example tablets, rings, tri-holes, extrudates etc., or as a granulate or powder. The mass ratio of palladium to promoter metal for example lies within a range of 1:5 to 3:1, preferably within a range of 1:4 to 2:1, and particularly preferably within a range of 1:3 to 1:1.

Suitable carrier substrates are $Al_2O_3$, $SiO_2$, alumo silicates, $TiO_2$, $ZrO_2$, ZnO, MgO, $Fe_2O_3$ and $CeO_2$, or mixtures thereof. In order to increase activity or selectivity the substrates can further be doped with at least one of the following elements: Li, Na, K, Rb, Cs, Be, Mg, Ca, Sr and/or Ba. Na, K and/or Ca are particularly suitable.

The BET surface area of the uncoated catalyst is ≤9 m$^2$/g, and more preferably ≤8 m$^2$/g, particularly preferably ≤6 m$^2$/g. The determination of the surface area may be carried out in accordance with ASTM D3663, Standard Test Method for Surface Area of Catalysts and Catalyst Carriers.

The integral pore volume of the catalyst (determined according to DIN 66134 of February 1998 ($N_2$ adsorption)) without the IL-coating preferably is in the range of 0.005 to 0.07 ml/g, more preferably in the range of 0.007 to 0.04 ml/g and particularly preferably within a range of 0.009 to 0.02 ml/g.

Suitable pre-formulated catalysts for use in preparing supported ionic liquid phase catalyst compositions of the invention include any commercially-available supported Pd or Pd/Ag catalysts supplied by, for example Süd-Chemie, AG, Munich, Germany, BASF, Johnson-Mathey, etc.

For the production of a catalyst composition of the invention a pre-formulated catalyst is loaded with ionic liquid. The ionic liquid to be used for this is not particularly restricted, and in principle, all known ionic liquids suitable for this purpose can be used. Preferred ionic liquids for use with this invention are compounds with the formula (I):

$$[A]_n^+[Y]_n^- \qquad (I),$$

wherein:

n=1 or 2;

[Y]$_n^-$ is selected from the group consisting of tetrafluoroborate ([$BF_4$]$^-$), hexafluorophosphate ([$PF_6$]$^-$), dicyanamide ([$N(CN)_2$]$^-$), halides (Cl$^-$, Br$^-$, F$^-$, I$^-$), hexafluoroantimonate ([$SbF_6$]$^-$), nitrate ([$NO_3$]$^-$), nitrite ([$NO_2$]$^-$), anionic metal complexes such as for example [$CuCl_4$]$^{2-}$, [$PdCl_4$]$^{2-}$ or [$AuCl_4$]$^-$, acetate ([$CH_3COO$]$^-$), trifluoracetate ([$F_3CCOO$]$^-$), hexafluoroarsenate ([$AsF_6$]$^-$), sulfate ([$SO_4$]$_2^-$), alkyl sulfates ([R'—$SO_4$]$^-$), tosylate ([$C_7H_7SO_3$]$^-$), triflate ([$CF_3SO_3$]$^-$), nonaflate ([$C_4F_9SO_3$]$^-$), triperfluoroethylene trifluorophosphate ([$PF_3(C_2F_5)_3$]$^-$), tricyanomethide ([$C(CN)_3$]$^-$), tetracyanoborate ([$B(CN)_4$]$^-$), thiocyanate ([SCN]$^-$), carbonate ([$CO_3$]$_2^-$), carboxylates ([R'—COO]$^-$), sulfonates ([R'$SO_3$]$^-$), dialkylphosphates ([R'$PO_4$R"]$^-$), alkyl phosphonates ([R'$HPO_3$]$^-$) and bissulfonylimides ([(R'—$SO_2$)$_2$N]$^-$), such as bis (trifluormethylsulfonyl)imide, wherein R' and R" are the same or different, and each represents a linear or branched, 1 to 12 carbon atom-containing aliphatic or alicyclic alkyl group or a $C_5$-$C_{18}$-aryl, $C_5$-$C_{18}$-aryl-$C_1$-$C_6$-alkyl, or $C_1$-$C_6$-alkyl-$C_5$-$C_{18}$-aryl group that can be substituted with halogen atoms; and

[A]$^+$ is selected from the group consisting of quaternary ammonium cations with the formula [NR$^1$R$^2$R$^3$R]$^+$, phosphonium cations with the formula [PR$^1$R$^2$R$^3$R]$^+$, sulfonium cations with the formula [SR$^1$R$^2$R]$^+$, guadinium cations with the formula (II):

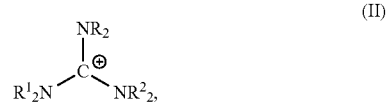

imidazolium cations with the formula (III)

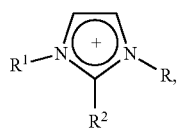
(III)

wherein the imidazole core may additionally be substituted with one or more groups selected from $C_1$-$C_6$-alkyl, $C_1$-$C_6$-alkoxy, $C_1$-$C_6$-aminoalkyl, $C_5$-$C_{12}$-aryl, and $C_5$-$C_{12}$-aryl-$C_1$-$C_6$-alkyl groups, pyridinium cations with the formula (IV)

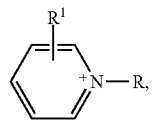
(IV)

wherein the pyridine core may additionally be substituted with one or more groups selected from $C_1$-$C_6$-alkyl, $C_1$-$C_6$-alkoxy, $C_1$-$C_6$-aminoalkyl, $C_5$-$C_{12}$-aryl, and $C_5$-$C_{12}$-aryl-$C_1$-$C_6$-alkyl groups, pyrazolium cations with the formula (V)

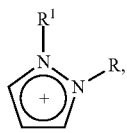
(V)

wherein the pyrazole core may additionally be substituted with one or more groups selected from $C_1$-$C_6$-alkyl, $C_1$-$C_6$-alkoxy, $C_1$-$C_6$-aminoalkyl, $C_5$-$C_{12}$-aryl, and $C_5$-$C_{12}$-aryl-$C_1$-$C_6$-alkyl groups, triazolium cations with the formula (VI)

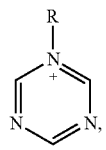
(VI)

wherein the triazole core may additionally be substituted with one or more groups selected from $C_1$-$C_6$-alkyl, $C_1$-$C_6$-alkoxy, $C_1$-$C_6$-aminoalkyl, $C_5$-$C_{12}$-aryl, and $C_5$-$C_{12}$-aryl-$C_1$-$C_6$-alkyl groups, and pyrrolidinium cations with the formula (VII)

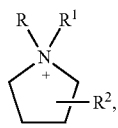
(VII)

wherein the pyrrolidinium core may additionally be substituted with one or more groups selected from $C_1$-$C_6$-alkyl, $C_1$-$C_6$-alkoxy, $C_1$-$C_6$-aminoalkyl, $C_5$-$C_{12}$-aryl, and $C_5$-$C_{12}$-aryl-$C_1$-$C_6$-alkyl groups, wherein $R^1$, $R^2$, and $R^3$ are selected independently from each other from the group consisting of: hydrogen; linear or branched, saturated or unsaturated, aliphatic or alicyclic alkyl groups with 1 to 20 carbon atoms, which may be interrupted by one or two of NH, O and/or S; heteroaryl groups with 3 to 8 carbon atoms and at least one hetero atom selected from N, O and S, wherein the heteroaryl groups can be substituted with one or more groups selected from $C_1$-$C_6$-alkyl groups and halogen atoms; heteroaryl-$C_1$-$C_6$-alkyl groups with 3 to 8 carbon atoms and at least one hetero atom selected from N, O and S in the heteroaryl portion, wherein the heteroaryl portion can be substituted with at least one group selected from $C_1$-$C_6$-alkyl groups and halogen atoms; polyethers with the formula [—$CH_2CH_2O$]$_n$$R^a$ with n=1 to 50,000, wherein $R^a$ is selected from the group consisting of linear or branched, saturated or unsaturated, aliphatic or alicyclic alkyl groups with 1 to 20 carbon atoms; aryl groups with 5 to 12 carbon atoms, which may be substituted with one or more $C_1$-$C_6$-alkyl groups and/or halogen atoms; aryl-$C_1$-$C_6$-alkyl groups with 5 to 12 carbon atoms in the aryl portion, which may be substituted with one or more $C_1$-$C_6$-alkyl groups and/or halogen atoms, and wherein R is selected from the group consisting of: linear or branched, saturated or unsaturated, aliphatic or alicyclic alkyl groups with 1 to 20 carbon atoms; heteroaryl-$C_1$-$C_6$-alkyl groups with 4 to 8 carbon atoms and at least one hetero atom selected from N, O and S in the heteroaryl portion, which may be substituted with one or more $C_1$-$C_6$-alkyl groups and/or halogen atoms; and aryl-$C_1$-$C_6$-alkyl groups with 4 to 12 carbon atoms in the aryl portion, which may be substituted with one or more $C_1$-$C_6$-alkyl groups and/or halogen atoms.

Further preferred ionic liquids for use with this invention are compounds with the formula (I):

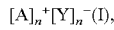

wherein:

n and [Y]$_n^-$ are as defined above, and

[A] is selected from the group consisting of quaternary ammonium cations with the formula [$NR^1R^2R^3R$]$^+$, imidazolium cations with the formula (III)

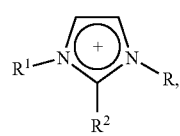
(III)

pyridinium cations with the formula (IV)

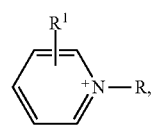
(IV)

and pyrrolidinium cations with the formula (VII)

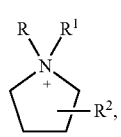
(VII)

wherein R, R$^1$, R$^2$ and R$^3$ are selected independently from each other from the group consisting of hydrogen; linear or branched C$_1$-C$_{12}$-alkyl groups; linear or branched (C$_1$-C$_6$-alkyloxy)-C$_1$-C$_6$-alkyl groups; and aryl-C$_1$-C$_6$-alkyl groups with 5 to 12 carbon atoms in the aryl portion, which may be substituted with one or more C$_1$-C$_6$-alkyl groups and/or halogen atoms.

More preferred ionic liquids for preparing supported ionic liquid phase catalysts of the invention include 1-butyl-3-methylimidazolium triflate, 1-ethyl-3-methylpyridinium ethylsulfate, 1-butyl-1-methylpyrrolidinium triflate, 1-butyl-2,3-dimethylimiclazolium triflate, 1-butyl-3-methylimidazolium tricyanomethane, 1-butyl-3-methylimidazolium methylsulfate, 1-butyl-3-methylimidazolium octylsulfate, 1-butyl-3-methylimidazolium tetrafluoroborate, 1-ethyl-3-methylimidazolium ethylsulfate, 1-ethyl-3-methylimidazolium methylphosphonate, 1-ethyl-3-methylimidazolium triflate, 1-butyl-1-methylpyrrolidinium bis(trifluoromethylsufonyl)imide, 1-butyl-1-methylpyrrolidinium tetracyanoborate, 1-butyl-1-methylpyrrolidinium tris(pentafluoroethyl)trifluorophosphate, 1-butyl-3-methylimidazolium bis(trifluoromethylsufonyl)imide, 1-butyl-3-methylimidazolium tricyanomethane, 1-ethyl-3-methylpyridinium bis(trifluoromethylsufonyl)imide, 1-ethyl-3-methylimidazolium tetracyanoborate, 1-ethyl-3-methylimidazolium tris(pentafluoroethyl)trifluorophosphate, 1-ethyl-3-methylpyridinium bis(trifluoromethylsufonyl)imide, 1-methyl-3-octylimidazolium triflate, ethyldimethyl-(2-methoxyethyl)ammonium tris(pentafluoroethyl)trifluorophosphate, tributylmethylammonium dicyanamide, tricyclohexyltetradecylphosphonium tris(pentafluoroethyl)trifluorophosphate, 1-ethyl-3-methylimidazolium bis(trifluoromethylsufonyl)imide, and mixtures thereof.

More preferred ionic liquids further include those of the formula (I), wherein [A]$_n^+$ is selected from the group consisting of 1-butyl-1-methylpyrrolidinium, 1-butyl-2,3-dimethylimidazolium, 1-butyl-3-methylimidazolium, 1-ethyl-3-methylimidazolium, 1-ethyl-3-methylpyridinium, 1-methyl-3-octylimidazolium, ethyldimethyl-(2-methoxyethyl)ammonium, tributylmethylammonium, tricyclohexyltetradecylphosphonium, and mixtures thereof, and wherein [Y]$_n^-$ is selected from the group consisting of bis(trifluoromethylsufonyl)imide, dicyanamide, ethylsulfate, methylphosphonate, methylsulfate, octylsulfate, tetracyanoborate, tetrafluoroborate, tricyanomethane, triflate, tris(pentafluoroethyl)trifluorophosphate, and mixtures thereof.

For the production of catalyst compositions of the invention, the ionic liquid or mixtures of several ionic liquids are dissolved or suspended in a solution agent suitable for the purpose, such as for example water, alcohols, acetone etc., or in a solution agent mixture, and applied continuously onto the already pre-formed catalyst inside a reaction chamber with the aid of a nozzle. For this the solution agent is continuously removed from the reaction chamber during the process. In order to achieve an even coating of the substrate, the substrate material is continuously fluidized through a process gas in a process known as fluidized bed coating. Further suitable coating processes are dip coating or spray application with a spray pistol or a spray drying pistol.

Apart from the application of ionic liquid by means of coating technologies, the same can also be applied by impregnating with a solution or suspension. For this the ionic liquid or mixtures of several ionic liquids are dissolved or suspended in a suitable solution agent (mixture) and subsequently brought into contact with the pre-formed catalyst. The solution agent is then removed under vacuum or at an increased temperature (or both), by resting in air, or by means of a gas stream. The quantity of solution agent used can be equal to or smaller or greater than the pore volume of the catalyst used.

The quantity of ionic liquid used is equal to or smaller than the pore volume of the catalyst used. After the application of the ionic liquid, one is left with an externally dry solid body coated with the desired quantity of ionic liquid. The pore volume of the resulting catalyst composition is reduced by the volume of the ionic liquid. Related to the total weight of the catalyst 0.01-10%, preferably 0.1-5 wt. %, more preferably 0.2-3 wt. %, and particularly preferably 0.3-1.5 wt. % of ionic liquid is used. The distribution of ionic liquid on the macroscopic substrate form body, granulate or powder is freely adjustable by selecting the coating conditions. Depending on the selection of the conditions, a formation of a so-called eggshell, egg-white, egg-yolk, or a uniform distribution of the ionic liquid may result on the substrate. In addition, any concentration gradient of ionic liquid can be created on the substrate. The ionic liquid is preferably applied to the substrate surface as a thin shell. The shell thickness of the ionic liquid on the substrate surface of this invention usually lies within a range of 10 to 2000 μm, preferably within a range of 20 to 1000 μm, and particularly preferably within a range of 50 to 250 μm.

The resulting catalyst can be used without restricting the target reaction. The reduction of metal particles required for activating the catalyst can either take place prior to a coating with the ionic liquid or following the same.

The catalyst can for example be reduced prior to coating with an ionic liquid. The methods to be used for the same are known to the expert, and can for example include wet chemical methods through reduction such as for example NaBH$_4$, LiAlH$_4$, hydrazine (hydrate), hypophosphite, formic acid, or salts of the same (formates). In addition a reduction can be brought about in the gaseous phase with hydrogen (in all mixtures with an inert gas; preferably 5% in N$_2$) within a temperature range of 50-200° C., preferably at 80-120° C.

The reduced metal particles obtained in this way usually have a diameter within a range of 1 to 30 nm, preferably within a range of 1 to 10 nm, and particularly preferably within a range of 2 to 8 nm.

EXAMPLES

Example 1

Sample A contains 0.017 wt % Pd on 1-2 mm alumina spheres with a BET surface area of 4.0 m$^2$/g. In order to make Sample A, 1100 g Alpha Alumina was added to 1075 mL PdCl$_2$ solution (0.178 mg Pd/mL) heated at 70° C. After the carrier was soaked in the solution for 1 hour, the solution was drained and then the catalyst was washed 10 times using 5 minute soak times with room temperature deionized water. After final wash, the catalyst was calcined in a muffle oven in air at 565° C. for 4 hours.

Sample A1 was made by adding 0.5 wt % of EMIM [EtSO$_4$] (1-ethyl-3-methylimidazolium ethylsulfate) on Sample A. In order to make Sample A1, Sample A (516.0 mg) was impregnated with an aqueous solution of 1-ethyl-3-methylimidazolium ethylsulfate (232 μL, 11.11 mg/mL) by incipient wetness. The catalyst was dried at 80° C. for 16 hours and reduced at 100° C. in 5% H$_2$/N$_2$ for 1 hour.

Sample A2 was made by adding 0.5 wt % of BMPr[OTf] (1-butyl-3-methylimidazolium triflate) on Sample A. In order to make Sample A2, Sample A (476.3 mg) was impregnated with an aqueous solution of 1-butyl-3-methylimidazolium triflate (214 μL, 11.11 mg/mL) by incipient wetness. The catalyst was dried at 80° C. for 16 hours and reduced at 100° C. in 5% H$_2$/N$_2$ for 1 hour.

Sample A3 was made by adding 0.5 wt % of BMPr[OTf] (1-butyl-1-methylpyrrolidinium triflate) on Sample A. In order to make Sample A3, Sample A (499.7 mg) was impregnated with an aqueous solution of 1-butyl-1-methylpyrrolidinium triflate (225 μL, 11.11 mg/mL) by incipient wetness. The catalyst was dried at 80° C. for 16 hours and reduced at 100° C. in 5% H$_2$/N$_2$ for 1 hour.

Sample A4 was made by adding 0.5 wt % of BMMIM [OTf] (1-Butyl-2,3-dimethylimidazolium triflate) on Sample A. In order to make Sample A4, Sample A (528.8 mg) was impregnated with an aqueous solution of 1-Butyl-2,3-dimethylimidazolium triflate (238 μL, 11.11 mg/mL) by incipient wetness. The catalyst was dried at 80° C. for 16 hours and reduced at 100° C. in 5% H$_2$/N$_2$ for 1 hour.

Sample A5 was made by adding 0.5 wt % of BMIM[BF$_4$] (1-butyl-3-methylimidazolium tetrafluoroborate) on Sample A. In order to make Sample A5, Sample A (508.2 mg) was impregnated with an aqueous solution of 1-butyl-3-methylimidazolium tetrafluoroborate (229 μL, 11.11 mg/mL) by incipient wetness. The catalyst was dried at 80° C. for 16 hours and reduced at 100° C. in 5% H$_2$/N$_2$ for 1 hour.

Sample A6 was made by adding 0.5 wt % of BMIM [MeSO$_4$] (1-butyl-3-methylimidazolium methylsulfate) on Sample A. In order to make Sample A6, Sample A (511.8 mg) was impregnated with an aqueous solution of 1-butyl-3-methylimidazolium methylsulfate (230 μL, 11.11 mg/mL) by incipient wetness. The catalyst was dried at 80° C. for 16 hours and reduced at 100° C. in 5% H$_2$/N$_2$ for 1 hour.

Sample A7 was made by adding 0.5 wt % of BMIM [C$_8$H$_{17}$SO$_4$] (1-butyl-3-methylimidazolium octylsulfate) on Sample A. In order to make Sample A7, Sample A (485.7 mg) was impregnated with an aqueous solution of 1-butyl-3-methylimidazolium octylsulfate (218 μL, 11.11 mg/mL) by incipient wetness. The catalyst was dried at 80° C. for 16 hours and reduced at 100° C. in 5% H$_2$/N$_2$ for 1 hour.

Sample A8 was made by adding 0.5 wt % of EMIM[OTf] (1-ethyl-3-methylimidazolium triflate) on Sample A. In order to make Sample A8, Sample A (509.9 mg) was impregnated with an aqueous solution of 1-ethyl-3-methylimidazolium triflate (229 μL, 11.11 mg/mL) by incipient wetness. The catalyst was dried at 80° C. for 16 hours and reduced at 100° C. in 5% H$_2$/N$_2$ for 1 hour.

Sample A9 was made by adding 0.5 wt % of EMPy [EtSO$_4$] (1-ethyl-3-methylpyridinium ethylsulfate) on Sample A. In order to make Sample A9, Sample A (504.0 mg) was impregnated with an aqueous solution of 1-ethyl-3-methylpyridinium ethylsulfate (227 μL, 11.11 mg/mL) by incipient wetness. The catalyst was dried at 80° C. for 16 hours and reduced at 100° C. in 5% H$_2$/N$_2$ for 1 hour.

Sample A10 was made by adding 0.5 wt % of EMIM [MePO$_3$] (1-ethyl-3-methylimidazolium methylphosphonate) on Sample A. In order to make Sample A10, Sample A (517.1 mg) was impregnated with an aqueous solution of 1-ethyl-3-methylimidazolium methylphosphonate (233 μL, 11.11 mg/mL) by incipient wetness. The catalyst was dried at 80° C. for 16 hours and reduced at 100° C. in 5% H$_2$/N$_2$ for 1 hour.

Sample A11 was made by adding 0.5 wt % of BMIM[C (CN)$_3$] (1-butyl-3-methylimidazolium tricyanomethane) on Sample A. In order to make Sample A11, Sample A (504.0 mg) was impregnated with a solution of 1-butyl-3-methylimidazolium bis(trifluoromethylsulfonyl)imide in 2-butanone (227 μL, 11.11 mg/mL) by incipient wetness. The catalyst was dried at 60° C. for 4 hours and reduced at 100° C. in 5% H$_2$/N$_2$ for 1 hour.

Sample A12 was made by adding 0.5 wt % of BMIM [NTf$_2$] (1-butyl-3-methylimidazolium bis(trifluoromethylsulfonyl)imide) on Sample A. In order to make Sample A12, Sample A (513.4 mg) was impregnated with a solution of 1-butyl-3-methylimidazolium bis(trifluoromethylsulfonyl)imide in 2-butanone (231 μL, 11.11 mg/mL) by incipient wetness. The catalyst was dried at 60° C. for 4 hours and reduced at 100° C. in 5% H$_2$/N$_2$ for 1 hour.

Sample A13 was made by adding 0.5 wt % of MOIM [OTf] (1-methyl-3-octylimidazolium triflate) on Sample A. In order to make Sample A13, Sample A (502.1 mg) was impregnated with a solution of 1-methyl-3-octylimidazolium triflate in 2-butanone (226 μL, 11.11 mg/mL) by incipient wetness. The catalyst was dried at 60° C. for 4 hours and reduced at 100° C. in 5% H$_2$/N$_2$ for 1 hour.

Sample A14 was made by adding 0.5 wt % of EMIM [NTf$_2$] (1-ethyl-3-methylimidazolium bis(trifluoromethylsulfonyl)imide) on Sample A. In order to make Sample A14, Sample A (490.3 mg) was impregnated with a solution of 1-ethyl-3-methylimidazolium bis(trifluoromethylsulfonyl)imide in 2-butanone (220 μL, 11.11 mg/mL) by incipient wetness. The catalyst was dried at 60° C. for 4 hours and reduced at 100° C. in 5% H$_2$/N$_2$ for 1 hour.

Sample A15 was made by adding 0.5 wt % of EMIM[B (CN)$_4$] (1-ethyl-3-methylimidazolium tetracyanoborate) on Sample A. In order to make Sample A15, Sample A (504.8 mg) was impregnated with a solution of 1-ethyl-3-methylimidazolium tetracyanoborate in 2-butanone (227 μL, 11.11 mg/mL) by incipient wetness. The catalyst was dried at 60° C. for 4 hours and reduced at 100° C. in 5% H$_2$/N$_2$ for 1 hour.

Sample A16 was made by adding 0.5 wt % of EMIM [PF$_3$(C$_2$F$_5$)$_3$] (1-ethyl-3-methylimidazolium tris(pentafluoroethyl)trifluorophosphate) on Sample A. In order to make Sample A16, Sample A (514.4 mg) was impregnated with a solution of 1-ethyl-3-methylimidazolium tris(pentafluoroethyl)trifluorophosphate in 2-butanone (231 μL, 11.11 mg/mL) by incipient wetness. The catalyst was dried at 60° C. for 4 hours and reduced at 100° C. in 5% H$_2$/N$_2$ for 1 hour.

Sample A17 was made by adding 0.5 wt % of EMPy [NTf2] (1-ethyl-3-methylpyridinium bis(trifluoromethylsulfonyl)imide) on Sample A. In order to make Sample A17, Sample A (531.6 mg) was impregnated with a solution of 1-ethyl-3-methylpyridinium bis(trifluoromethylsulfonyl)imide in 2-butanone (239 μL, 11.11 mg/mL) by incipient wetness. The catalyst was dried at 60° C. for 4 hours and reduced at 100° C. in 5% H$_2$/N$_2$ for 1 hour.

Sample A18 was made by adding 0.5 wt % of BMPr [NTf$_2$] (1-butyl-1-methylpyrrolidinium bis(trifluoromethylsulfonyl)imide) on Sample A. In order to make Sample A18, Sample A (512.5 mg) was impregnated with a solution of 1-butyl-1-methylpyrrolidinium bis(trifluoromethylsulfonyl) imide in 2-butanone (230 µL, 11.11 mg/mL) by incipient wetness. The catalyst was dried at 60° C. for 4 hours and reduced at 100° C. in 5% $H_2/N_2$ for 1 hour.

Sample A19 was made by adding 0.5 wt % of BMPr[$PF_3$ $(C_2F_5)_3$] (1-butyl-1-methylpyrrolidinium tris(pentafluoroethyl)trifluorophosphate) on Sample A. In order to make Sample A19, Sample A (510.3 mg) was impregnated with a solution of 1-butyl-1-methylpyrrolidinium tris(pentafluoroethyl)trifluorophosphate in 2-butanone (229 µL, 11.11 mg/mL) by incipient wetness. The catalyst was dried at 60° C. for 4 hours and reduced at 100° C. in 5% $H_2/N_2$ for 1 hour.

Sample A20 was made by adding 0.5 wt % of BMPr[B(CN)$_4$] (1-butyl-1-methylpyrrolidinium tetracyanoborate) on Sample A. In order to make Sample A20, Sample A (516.0 mg) was impregnated with a solution of 1-butyl-1-methylpyrrolidinium tetracyanoborate in 2-butanone (232 µL, 11.11 mg/mL) by incipient wetness. The catalyst was dried at 60° C. for 4 hours and reduced at 100° C. in 5% $H_2/N_2$ for 1 hour.

Sample A21 was made by adding 0.5 wt % of TBMA[N(CN)$_2$] (tributylmethylammonium dicyanamide) on Sample A. In order to make Sample A21, Sample A (474.2 mg) was impregnated with a solution of tributylmethylammonium dicyanamide in 2-butanone (213 µL, 11.11 mg/mL) by incipient wetness. The catalyst was dried at 60° C. for 4 hours and reduced at 100° C. in 5% $H_2/N_2$ for 1 hour.

Sample A22 was made by adding 0.5 wt % of {EtMe$_2$(MeOEt)}N[$PF_3(C_2F_5)_3$] (ethyldimethyl-(2-methoxyethyl) ammonium tris(pentafluoroethyl)trifluorophosphate) on Sample A. In order to make Sample A22, Sample A (477.6 mg) was impregnated with a solution of ethyldimethyl-(2-methoxyethyl)ammonium tris(pentafluoroethyl)trifluorophosphate in 2-butanone (215 µL, 11.11 mg/mL) by incipient wetness. The catalyst was dried at 60° C. for 4 hours and reduced at 100° C. in 5% $H_2/N_2$ for 1 hour.

Example 2

Sample B1 was made by adding 0.001 wt % of EMIM [EtSO$_4$] (1-ethyl-3-methylimidazolium ethylsulfate) on Sample A. In order to make Sample B1, Sample A (485.8 mg) was impregnated with an aqueous solution of 1-ethyl-3-methylimidazolium ethylsulfate (219 µL, 0.022 mg/mL) by incipient wetness. The catalyst was dried at 80° C. for 16 hours and reduced at 100° C. in 5% $H_2/N_2$ for 1 hour.

Sample B2 was made by adding 0.007 wt % of EMIM [EtSO$_4$] (1-ethyl-3-methylimidazolium ethylsulfate) on Sample A. In order to make Sample B2, Sample A (505.1 mg) was impregnated with an aqueous solution of 1-ethyl-3-methylimidazolium ethylsulfate (227 µL, 0.16 mg/mL) by incipient wetness. The catalyst was dried at 80° C. for 16 hours and reduced at 100° C. in 5% $H_2/N_2$ for 1 hour.

Sample B3 was made by adding 0.025 wt % of EMIM [EtSO$_4$] (1-ethyl-3-methylimidazolium ethylsulfate) on Sample A. In order to make Sample B3, Sample A (512.8 mg) was impregnated with an aqueous solution of 1-ethyl-3-methylimidazolium ethylsulfate (231 µL, 0.56 mg/mL) by incipient wetness. The catalyst was dried at 80° C. for 16 hours and reduced at 100° C. in 5% $H_2/N_2$ for 1 hour.

Sample B4 was made by adding 0.05 wt % of EMIM [EtSO$_4$] (1-ethyl-3-methylimidazolium ethylsulfate) on Sample A. In order to make Sample B4, Sample A (468.0 mg) was impregnated with an aqueous solution of 1-ethyl-3-methylimidazolium ethylsulfate (210 µL, 1.11 mg/mL) by incipient wetness. The catalyst was dried at 80° C. for 16 hours and reduced at 100° C. in 5% $H_2/N_2$ for 1 hour.

Sample B5 was made by adding 0.1 wt % of EMIM [EtSO$_4$] (1-ethyl-3-methylimidazolium ethylsulfate) on Sample E. In order to make Sample B5, Sample A (497.3 mg) was impregnated with an aqueous solution of 1-ethyl-3-methylimidazolium ethylsulfate (224 µL, 2.22 mg/mL) by incipient wetness. The catalyst was dried at 80° C. for 16 hours and reduced at 100° C. in 5% $H_2/N_2$ for 1 hour.

Sample B6 was made by adding 0.25 wt % of EMIM [EtSO4] (1-ethyl-3-methylimidazolium ethylsulfate) on Sample A. In order to make Sample B6, Sample A (480.9 mg) was impregnated with an aqueous solution of 1-ethyl-3-methylimidazolium ethylsulfate (216 µL, 5.56 mg/mL) by incipient wetness. The catalyst was dried at 80° C. for 16 hours and reduced at 100° C. in 5% $H_2/N_2$ for 1 hour.

Comparative Example 3

Comparative Sample C contains 0.019 wt % Pd on 1-2 mm alumina spheres with a BET surface area of 50 $m^2/g$. In order to make Comparative Sample C, 10 g alumina was added to 11.4 mL $PdCl_2$ solution (0.1667 mg Pd/mL) heated at 70° C. After the carrier was soaked in the solution for 1 hour, the solution was withdrawn and then the catalyst was washed 10 times using 5 minute soak times with room temperature deionized water. After the final washing step, the catalyst was calcined in muffle oven in air at 565° C. for 4 hours.

Comparative Sample C1 was made by adding 0.5 wt % of EMIM[EtSO$_4$] (1-ethyl-3-methylimidazolium ethylsulfate) on Comparative Sample C. In order to make Comparative Sample C1, Comparative Sample C (502.1 mg) was impregnated with an aqueous solution of 1-ethyl-3-methylimidazolium ethylsulfate (316 µL, 7.94 mg/mL) by incipient wetness. The catalyst was dried at 80° C. for 16 hours and reduced at 100° C. in 5% $H_2/N_2$ for 1 hour.

Comparative Sample C2 was made by adding 0.5 wt % of BMIM[OTf] (1-butyl-3-methylimidazolium triflate) on Comparative Sample C. In order to make Comparative Sample C2, Comparative Sample C (484.4 mg) was impregnated with an aqueous solution of 1-butyl-3-methylimidazolium triflate (305 µL, 7.94 mg/mL) by incipient wetness. The catalyst was dried at 80° C. for 16 hours and reduced at 100° C. in 5% $H_2/N_2$ for 1 hour.

Example 4

Sample A, Samples A1-A22, Samples B1-B6, and Comparative Samples C, C1 and C2 were tested as prepared in a microreactor test unit at typical front-end hydrogenation conditions. In the test, a simulated de-propanizer feed containing 0.35 mol % acetylene, 15 mol % hydrogen, 0.02 mol % CO, 47 mol % ethylene, and balance nitrogen was passed over a 260 µl catalyst bed at 478 psig (34 bar) in total pressure and 7000 $h^{-1}$ in Gas Hourly Space Velocity (GHSV), while the bed temperature was gradually increased from about 45° C. The acetylene concentration at the reactor outlet was monitored with an on-line gas chromatograph (GC). The acetylene concentration at reactor outlet continued decreasing with increasing temperature until reaching <25 ppm. The temperature at this point was defined as the "clean up temperature" (T1). Catalyst bed temperature was further increased until 125° C. (the maximum temperature the test unit could reach) or a certain temperature (T2), at which the outlet ethane concentration was >2% due to the increased non-selective reaction of hydrogen with ethylene.

The temperature range between T1 and T2 is called the "operation window". Test results of Sample A, Samples A1 to A22, Samples B1-B6, as well as of Comparative Sample C, C1-C2 are listed in the table below. For catalysts that did not run away at the maximum temperature the test unit could reach, T2 was calculated by fitting the data at temperatures above complete acetylene conversion with a first order kinetic model.

Test Results of Samples A, A1 to A22, B1 to B6, and Comparative Samples C and C1 to C2

|  | T1 [° C.] | T2 [° C.] | Operation Window [° C.] | Selectivity at T1 [%] | Ethane Make at 125° C. |
|---|---|---|---|---|---|
| Sample A | 63 | 84 | 21 | 92.8 | 10.439 |
| Sample A1 | 68 | 176 | 108 | 96.1 | 0.429 |
| Sample A2 | 68 | 137 | 69 | 96.9 | 0.714 |
| Sample A3 | 61 | 113 | 52 | 89.0 | 3.316 |
| Sample A4 | 62 | 113 | 51 | 85.6 | 3.228 |
| Sample A5 | 69 | 164 | 95 | 94.5 | 0.462 |
| Sample A6 | 68 | 167 | 99 | 97.6 | 0.390 |
| Sample A7 | 68 | 157 | 89 | 95.5 | 0.594 |
| Sample A8 | 65 | 141 | 76 | 96.2 | 1.139 |
| Sample A9 | 65 | 100 | 35 | 95.8 | 9.45 |
| Sample A10 | 82 | 188 | 106 | 90.1 | 0.194 |
| Sample A11 | 68 | 157 | 89 | 90.0 | 0.637 |
| Sample A12 | 61 | 100 | 39 | 89.5 | 4.668 |
| Sample A13 | 67 | 115 | 48 | 66.1 | 3.005 |
| Sample A14 | 60 | 110 | 50 | 99.8 | 3.477 |
| Sample A15 | 71 | 149 | 78 | 90.6 | 0.821 |
| Sample A16 | 67 | 145 | 78 | 90.1 | 1.199 |
| Sample A17 | 62 | 86 | 24 | 93.0 | 10.23 |
| Sample A18 | 64 | 101 | 37 | 88.9 | 4.836 |
| Sample A19 | 62 | 120 | 58 | 74.8 | 2.382 |
| Sample A20 | 69 | 150 | 81 | 98.9 | 0.906 |
| Sample A21 | 65 | 153 | 88 | 85.2 | 0.982 |
| Sample A22 | 66 | 122 | 56 | 93.2 | 2.315 |
| Sample B1 | 62 | 82 | 20 | 47.3 | 10.444 |
| Sample B2 | 63 | 101 | 38 | 69.0 | 8.691 |
| Sample B3 | 60 | 113 | 53 | 96.3 | 9.122 |
| Sample B4 | 61 | 119 | 58 | 95.5 | 5.378 |
| Sample B5 | 65 | 121 | 56 | 98.4 | 3.838 |
| Sample B6 | 67 | 123 | 56 | 100 | 2.428 |
| Comparative Sample C | 56 | 76 | 20 | 91.1 | 10.506 |
| Comparative Sample C1 | 68 | 99 | 31 | 81.3 | 5.725 |
| Comparative Sample C2 | 65 | 98 | 33 | 96.1 | 6.878 |

The operation window as well as the selectivity markedly increase with decrease in BET surface area (Samples A1 and A2 compared to Comparative Samples C1 and C2).

Example 5

Sample D is a commercial selective hydrogenation catalyst that is supplied by Süd-Chemie AG under trade name OleMax® 251. It contains 0.019 wt % Pd and 0.05 wt % Ag on 4×4 mm alumina tablets with a BET surface area of about 4.0 m²/g.

Sample D1 was made by adding 0.5 wt % of BMMIM [OTf] (1-Butyl-2,3-dimethylimidazolium triflate) on Sample D. In order to make Sample D1, 0.6 g of the ionic liquid BMMIM[OTf] were dissolved in 150 ml deionized water. At the same time 120 g of the dry Sample D is fluidized in a reaction chamber with synthetic air as the process gas. The solution of BMMIM[OTf] in water was introduced into the reaction chamber at a flow rate of 5 ml/min via a feed pump and sprayed onto the solid catalyst via a spray nozzle at a temperature of 80° C. Once the entire solution has been applied and the substrate is dry, the catalyst formulation is further dried at 80° C. for 2 hours.

Sample D2 was made by adding 1.0 wt % of BMMIM [OTf] (1-Butyl-2,3-dimethylimidazolium triflate) on Sample D. In order to make Sample D2, 1.2 g of the ionic liquid BMMIM[OTf] were dissolved in 150 ml deionized water. At the same time 120 g of the dry Sample D is fluidized in a reaction chamber with synthetic air as the process gas. The solution of BMMIM[OTf] in water was introduced into the reaction chamber at a flow rate of 5 ml/min via a feed pump and sprayed onto the solid catalyst via a spray nozzle at a temperature of 80° C. Once the entire solution has been applied and the substrate is dry, the catalyst formulation is further dried at 80° C. for 2 hours.

Sample D3 was made by adding 2.0 wt % of BMMIM [OTf] (1-Butyl-2,3-dimethylimidazolium triflate) on Sample D. In order to make Sample D3, 2.4 g of the ionic liquid BMMIM[OTf] were dissolved in 150 ml deionized water. At the same time 120 g of the dry Sample D is fluidized in a reaction chamber with synthetic air as the process gas. The solution of BMMIM[OTf] in water was introduced into the reaction chamber at a flow rate of 5 ml/min via a feed pump and sprayed onto the solid catalyst via a spray nozzle at a temperature of 80° C. Once the entire solution has been applied and the substrate is dry, the catalyst formulation is further dried at 80° C. for 2 hours.

Sample D4 was made by adding 3.0 wt % of BMMIM [OTf] (1-Butyl-2,3-dimethylimidazolium triflate) on Sample D. In order to make Sample D4, 3.6 g of the ionic liquid BMMIM[OTf] were dissolved in 150 ml deionized water. At the same time 120 g of the dry Sample D is fluidized in a reaction chamber with synthetic air as the process gas. The solution of BMMIM[OTf] in water was introduced into the reaction chamber at a flow rate of 5 ml/min via a feed pump and sprayed onto the solid catalyst via a spray nozzle at a temperature of 80° C. Once the entire solution has been applied and the substrate is dry, the catalyst formulation is further dried at 80° C. for 2 hours.

Sample D1' was made by impregnation of Sample D with a BMMIM[OTf] (1-Butyl-2,3-dimethylimidazolium triflate) solution containing 0.5 g of BMMIM[OTf] in 38 ml deionized water. The clear solution is added to 120 g of dry Sample D. The mixture is then mixed at room temperature for approx. 60 minutes. The catalyst formulation is then dried at 80° C. for 16 h to finally obtain Sample D1'.

Example 6

Samples prepared in Example 5 were tested as prepared in a bench scale test unit at typical front-end hydrogenation conditions. In the test, a simulated de-ethanizer feed containing 0.35 mol % acetylene, 20 mol % hydrogen, 0.02 mol % CO, 45 mol % ethylene, and balance methane was passed over a 25 ml catalyst bed at 500 psig (35.5 bar) in total pressure and 7000 h$^{-1}$ in Gas Hourly Space Velocity (GHSV), while the bed temperature was gradually increased from about 35° C. The acetylene concentration at the reactor outlet was monitored with an on-line gas chromatograph (GC). The acetylene concentration at reactor outlet continued decreasing with increasing temperature until reaching <25 ppm. The temperature at this point was defined as the "clean up temperature" (T1). Catalyst bed temperature was further increased until 105° C. (the maximum temperature the water bath could reach) or a certain temperature (T2), at which the outlet ethane concentration was >2% due to the increased non-selective reaction of hydrogen with ethylene. The temperature range between T1 and T2 is called the "operation window". Test results of Sample D and Samples D1 to D4 and D1' are listed in the table below.

Front End Deethanizer Feed Test Results

|  | T1 [° C.] | T2 [° C.] | Operation Window [° C.] | Selectivity at T1 [%] |
|---|---|---|---|---|
| Sample D | 52 | 57 | 5 | −1 |
| Sample D1 | 61 | 97 | 36 | 52 |
| Sample D2 | 61 | 105 | 44 | 61 |
| Sample D3 | 69 | >105 | >36 | 48 |
| Sample D4 | 73 | >105 | >32 | 56 |
| Sample D1' | 67 | 99 | 32 | 38 |

The operation window as well as the selectivity markedly increase with increasing BMMIM[OTf] content. The optimum BMMIM[OTf] loading seems to be 0.5-1%. At higher loading, the runaway temperature continued to increase at the expense of a higher T1 temperature. Adding BMMIM [OTf] onto Sample D can be realized by coating or wet impregnation; and both methods can generate a new catalyst with significantly improved operation window.

Example 7

Sample E is a commercial front end selective hydrogenation catalyst that is supplied by Süd-Chemie AG under the trade name OleMax® 250. It contains 0.018 wt % Pd on 4×4 mm alumina tablets with a BET surface area of about 4.0 m$^2$/g.

Sample E1 was made by adding 1.0 wt % of BMMIM [OTf] (1-Butyl-2,3-dimethylimidazolium triflate) on Sample E. In order to make Sample E1, 1.2 g of the ionic liquid BMMIM[OTf] were dissolved in 150 ml deionized water. At the same time 120 g of the dry Sample E is fluidized in a reaction chamber with synthetic air as the process gas. The solution of BMMIM[OTf] in water was introduced into the reaction chamber at a flow rate of 5 ml/min via a feed pump and sprayed onto the solid catalyst via a spray nozzle at a temperature of 80° C. Once the entire solution has been applied and the substrate is dry, the catalyst formulation is further dried at 80° C. for 2 hours.

Sample E2 was made by adding 2.0 wt % of BMMIM [OTf] (1-Butyl-2,3-dimethylimidazolium triflate) on Sample E. In order to make Sample E2, 2.4 g of the ionic liquid BMMIM[OTf] were dissolved in 150 ml deionized water. At the same time 120 g of the dry Sample E is fluidized in a reaction chamber with synthetic air as the process gas. The solution of BMMIM[OTf] in water was introduced into the reaction chamber at a flow rate of 5 ml/min via a feed pump and sprayed onto the solid catalyst via a spray nozzle at a temperature of 80° C. Once the entire solution has been applied and the substrate is dry, the catalyst formulation is further dried at 80° C. for 2 hours.

Sample E3 was made by adding 3.0 wt % of BMMIM [OTf] (1-Butyl-2,3-dimethylimidazolium triflate) on Sample E. In order to make Sample E3, 3.6 g of the ionic liquid BMMIM[OTf] were dissolved in 150 ml deionized water. At the same time 120 g of the dry Sample E is fluidized in a reaction chamber with synthetic air as the process gas. The solution of BMMIM[OTf] in water was introduced into the reaction chamber at a flow rate of 5 ml/min via a feed pump and sprayed onto the solid catalyst via a spray nozzle at a temperature of 80° C. Once the entire solution has been applied and the substrate is dry, the catalyst formulation is further dried at 80° C. for 2 hours.

Example 8

Sample E, Sample E1, Sample E2 and Sample E3 were tested after in-situ reduction at 94° C. for 1 hour in a bench scale test unit at typical front-end hydrogenation conditions. In the test, a simulated de-ethanizer feed containing 0.35 mol % acetylene, 20 mol % hydrogen, 0.02 mol % CO, 45 mol % ethylene, and balance methane was passed over a 25 ml catalyst bed at 500 psig (35.5 bar) in total pressure and 7000$^{-1}$ in Gas Hourly Space Velocity (GHSV), while the bed temperature was gradually increased from about 35° C. The acetylene concentration at the reactor outlet was monitored with an on-line gas chromatograph (GC). The acetylene concentration at reactor outlet continued decreasing with increasing temperature until reaching <25 ppm. The temperature at this point was defined as the "clean up temperature" (T1). Catalyst bed temperature was further increased until 105° C. (the maximum temperature the water bath could reach) or a certain temperature (T2), at which the outlet ethane concentration was >2% due to the increased non-selective reaction of hydrogen with ethylene. The temperature range between T1 and T2 is called the "operation window". Test results of Sample E and Samples E1 to E3 are listed in the table below.

Test Results of Sample E and Samples E1 to E3

|  | T1 [° C.] | T2 [° C.] | Operation Window [° C.] | Selectivity at T1 [%] |
|---|---|---|---|---|
| Sample E | 53 | 62 | 9 | 58 |
| Sample E1 | 53 | 69 | 16 | 65 |
| Sample E2 | 52 | 81 | 29 | 74 |
| Sample E3 | 62 | 92 | 30 | 78 |

Upon addition of BMMIM[OTf] onto the Pd/alumina catalyst, the operation window increases linearly up to a loading of 2% and then stays constant at 30° C. At higher loading, both T1 and operation window increased.

Example 9

Comparative Sample F is a commercial selective hydrogenation catalyst that is supplied by Süd-Chemie AG under trade name OleMax® 201. It contains 0.03 wt % Pd and 0.18 wt % Ag on 2-4 mm alumina spheres with a BET surface area of about 35 m$^2$/g.

Comparative Sample F1' was made by adding 0.5 wt % of EMIM[EtSO$_4$] (1-ethyl-3-methylimidazolium ethylsulfate) onto Sample F by incipient wetness impregnation method. The EMIM[EtSO$_4$] solution contains 0.5 g of EMIM[EtSO$_4$] in 60 ml deionized water. The clear solution was added to 100 g of Comparative Sample F and mixed for about 5 min. The catalyst formulation is then dried at 80° C. for 16 hr to obtain the final product.

Comparative Sample F2' was made by adding 1.0 wt % of EMIM[EtSO$_4$] (1-ethyl-3-methylimidazolium ethylsulfate) onto Sample F by incipient wetness impregnation method. The EMIM[EtSO$_4$] solution contains 1 g of EMIM[EtSO$_4$] in 60 ml deionized water. The clear solution was added to 100 g of Comparative Sample F and mixed for about 5 min. The catalyst formulation is then dried at 80° C. for 16 hr to obtain final product.

Sample D2' was made by adding 0.5 wt % EMIM[EtSO$_4$] (1-ethyl-3-methylimidazolium ethylsulfate) on Sample D by incipient wetness impregnation. The EMIM[EtSO$_4$] solution contains 0.5 g of EMIM[EtSO$_4$] in 24 ml deionized water.

The clear solution was added to 100 g of Sample D and mixed for about 5 min. The catalyst formulation is then dried at 80° C. for 16 hr to obtain final product.

Sample D3' was made by adding 1 wt % EMIM[EtSO$_4$] (1-ethyl-3-methylimidazolium ethylsulfate) on Sample D by incipient wetness impregnation. The EMIM[EtSO$_4$] solution contains 1 g of EMIM[EtSO$_4$] in 24 ml deionized water. The clear solution was added to 100 g of Sample D and mixed for about 5 min. The catalyst formulation is then dried at 80° C. for 16 hr to obtain final product.

Example 10

Samples and Comparative Samples prepared in Example 9 were tested as prepared in a bench scale test unit at typical front-end hydrogenation conditions. In the test, a simulated de-ethanizer feed containing 0.35 mol % acetylene, 20 mol % hydrogen, 0.02 mol % CO, 45 mol % ethylene, and balance methane was passed over a 25 ml catalyst bed at 500 psig (35.5 bar) in total pressure and 7000 h$^{-1}$ in Gas Hourly Space Velocity (GHSV), while the bed temperature was gradually increased from about 35° C. The acetylene concentration at the reactor outlet was monitored with an on-line gas chromatograph (GC). The acetylene concentration at reactor outlet continued decreasing with increasing temperature until reaching <25 ppm. The temperature at this point was defined as the "clean up temperature" (T1). Catalyst bed temperature was further increased until 105° C. (the maximum temperature the water bath could reach) or a certain temperature (T2), at which the outlet ethane concentration was >2% due to the increased non-selective reaction of hydrogen with ethylene. The temperature range between T1 and T2 is called the "operation window". Test results of Sample F2' and F3' did not run away at the maximum temperature the test unit could reach: the ethane make was 0.35% at 102° C. for both catalysts. Their T2's for 2% ethane make were calculated by fitting the data at temperatures above complete acetylene conversion with a first order kinetic model.

| Front End Deethanizer Feed Test Results | | | | |
|---|---|---|---|---|
| | T1 [° C.] | T2 [° C.] | T2 − T1 [° C.] | Selectivity at T1 [%] | Ethane Make at 102° C. [%] |
| Sample F | 51 | 53 | 2 | −5 | Not operable |
| Sample F1' | 54 | 75 | 21 | 76 | Not operable |
| Sample F2' | 59 | 80 | 21 | 86 | Not operable |
| Sample D | 52 | 57 | 5 | −1 | Not operable |
| Sample D2' | 65 | 148 | 83 | 91 | 0.35 |
| Sample D3' | 66 | 149 | 83 | 94 | 0.35 |

It appears that EMIM[EtSO$_4$] has much lower impact on Sample F than on Sample D.

What is claimed:

1. A heterogeneous shell catalyst for selective hydrogenation of unsaturated hydrocarbons, the heterogeneous shell catalyst comprising:
   (i) a porous solid substrate having an uncoated BET surface area of less than 9 m$^2$/g and an integral pore volume of 0.007 to 0.04 ml/g;
   (ii) a metal or metal-alloy shell comprising palladium included on the substrate having a thickness of 100 μm to 500 μm; and
   (iii) 0.1% to 5% by weight of the heterogeneous shell catalyst of one or more ionic liquids deposited within a pore surface of the porous solid substrate having the integral pore volume in a quantity that is less than the integral pore volume to provide an ionic liquid shell that is between 10 μm thick and 2000 μm thick, wherein a total quantity of the one or more ionic liquids used is between 0.01% to 5% by weight of the heterogeneous shell catalyst,
   wherein the one or more ionic liquids consist of one or more compounds of the formula:

$[A]_n^+[Y]_n^-$, wherein:
   n=1 or 2;
   $[A]_n^+$ comprises an imidazolium cation of the formula (III)

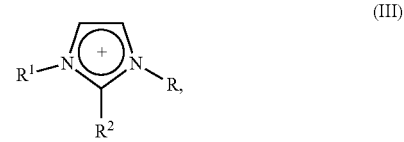

wherein R, R$^1$, and R$^2$ are independently selected from the group consisting of hydrogen and linear or branched C$_1$-C$_{12}$-alkyl groups, or $[A]_n^+$ is selected from the group consisting of 1-butyl-1-methylpyrrolidinium, 1-ethyl-3-methylpyridinium, ethyldimethyl-(2-methoxyethyl)-ammonium, tributylmethylammonium, tricyclohexyltetradecylphosphonium, and mixtures thereof; and
   wherein $[Y]_n^-$ is selected from the group consisting of bis(trifluoromethylsufonyl)imide, dicyanamide, ethylsulfate, methylphosphonate, methylsulfate, octylsulfate, tetracyanoborate, tetrafluoroborate, tricyanomethane, triflate, tris(pentafluoroethyl)trifluorophosphate, and mixtures thereof.

2. The heterogeneous shell catalyst of claim 1, wherein said BET surface area is within a range of 2 to 8 m$^2$/g.

3. The heterogeneous shell catalyst of claim 1, wherein the metal or metal alloy shell further comprises a promoter selected from the group consisting of Ag, Au, Zn, Sn, Cd, Pb, Cu, Bi, K, Ga, and mixtures thereof.

4. The heterogeneous shell catalyst of claim 3, wherein the promoter comprises Ag.

5. The heterogeneous shell catalyst of claim 3, having a ratio of palladium:promoter of 1:5 to 3:1.

6. The heterogeneous shell catalyst of claim 1, having a palladium loading of 10 to 1000 ppm.

7. The heterogeneous shell catalyst of claim 1, wherein $[A]^+$ is selected from the group consisting of 1-butyl-1-methylpyrrolidinium, 1-butyl-2,3-dimethylimidazolium, 1-butyl-3-methylimidazolium, 1-ethyl-3-methylimidazolium, 1-ethyl-3-methylpyridinium, 1-methyl-3-octylimidazolium, ethyldimethyl-(2-methoxyethyl)ammonium, tributylmethylammonium, tricyclohexyltetradecylphosphonium, and mixtures thereof.

8. The heterogeneous shell catalyst of claim 1, wherein the ionic liquid comprises one or more selected from the group consisting of 1-butyl-3-methylimidazolium triflate, 1-ethyl-3-methylpyridinium ethylsulfate, 1-butyl-1-methylpyrrolidinium triflate, 1-butyl-2,3-dimethylimidazolium triflate, 1-butyl-3-methylimidazolium tricyanomethane, 1-butyl-3-methylimidazolium methylsulfate, 1-butyl-3-methylimidazolium octylsulfate, 1-butyl-3-methylimidazolium tetrafluoroborate, 1-ethyl-3-methylimidazolium ethylsulfate, 1-ethyl-3-methylimidazolium methylphosphonate, 1-ethyl-3-methylimidazolium triflate, 1-butyl-1-methylpyrrolidinium bis(trifluoromethylsufonyl)imide, 1-butyl-1-methylpyrrolidinium tetracyanoborate, 1-butyl-1-methylpyrrolidinium tris(pentafluoroethyl)trifluorophosphate, 1-butyl-3-methylimidazolium bis(trifluoromethylsufonyl)imide, 1-ethyl-3-methylpyridinium bis(trifluoromethylsufonyl)imide, 1-ethyl-3-methylimidazolium tetracyanoborate, 1-ethyl-3-methylimidazolium tris(pentafluoroethyl)trifluorophosphate, 1-methyl-3-octylimidazolium triflate, ethyldimethyl-(2-methoxyethyl)ammonium tris(pentafluoroethyl)trifluorophosphate, tributylmethylammonium dicyanamide, tricyclohexyltetradecylphosphonium tris(pentafluoroethyl)trifluorophosphate, 1-ethyl-3-methylimidazolium bis(trifluoromethylsufonyl)imide, and mixtures thereof.

9. The heterogeneous shell catalyst of claim 1, having an ionic liquid loading of 0.1% to 5% by weight.

10. The heterogeneous shell catalyst of claim 1, further having a cleanup temperature of less than 80° C. and an operating window of greater than 25° C. when tested with a simulated de-ethanizer feed containing 0.35 mol % acetylene, 20 mol % hydrogen, 0.02 mol % CO, 45 mol % ethylene, and balance methane being passed over a 25 ml catalyst bed at 500 psig (35.5 bar) in total pressure and 7000 $h^{-1}$ in Gas Hourly Space Velocity (GHSV), while the bed temperature is gradually increased from about 35° C., the "clean up temperature" is defined as the temperature at which the outlet reaches <25 ppm acetylene, the runaway temperature is defined as the temperature at which the outlet ethane concentration is >2% and the operation window is defined as the difference between the runaway temperature and the clean up temperature.

11. The heterogeneous shell catalyst of claim 1, wherein the integral pore volume of the heterogeneous shell catalyst without the presence of said one or more ionic liquids is in the range of 0.009 to 0.02 ml/g.

12. The heterogeneous shell catalyst of claim 1, wherein the one or more ionic liquids are deposited on the substrate in an eggshell distribution.

13. The heterogeneous shell catalyst of claim 1, wherein the one or more ionic liquids are deposited such that a body of the heterogenous shell catalyst is externally dry.

* * * * *